United States Patent [19]

Herr et al.

[11] Patent Number: 4,741,998

[45] Date of Patent: May 3, 1988

[54] MONOCLONAL ANTIBODY TO MHS-5: A NEW PROBE FOR SEXUAL ASSAULT ANALYSES

[75] Inventors: John C. Herr; Mark Sigman; William M. Sutherland, all of Charlottesville, Va.

[73] Assignee: The University of Virginia Alumni Patents Foundation, Charlottesville, Va.

[21] Appl. No.: 741,601

[22] Filed: Jun. 5, 1985

[51] Int. Cl.$^4$ .......................... C07K 15/00; C12N 5/00; G01N 33/535; G01N 33/577

[52] U.S. Cl. .......................................... 435/7; 435/28; 435/68; 435/70; 435/172.2; 435/240.27; 435/810; 435/948; 436/518; 436/543; 436/547; 436/548; 436/808; 530/387; 935/104; 935/108; 935/110

[58] Field of Search ...................... 435/68, 172.2, 810, 435/948, 240, 7, 70, 241, 28; 260/112 R; 935/95, 99, 108, 110, 100, 102-104; 436/548, 516, 543, 808, 547; 530/387, 388; 514/2

[56] References Cited

U.S. PATENT DOCUMENTS 4,511,661  4/1985  Goldberg .............................. 435/68

OTHER PUBLICATIONS

Herr, J. C. et al., Biol. Reprod. 32(3): 695-712 (1985) cited in Bio. Abstract 80013306.

Uhlenbruck, G. et al., Hoppe-Seyler's 2 Physiol. Chem. 365(6): 613-618 (1984) cited in Bio. Abstract 78079607.

Taylor, E. H. et al., Ann. Clin. Lab. Sci. 14(1): 21-26 (1984) cited in Bio. Abstract 78004408.

Lad, P. M. et al., Biochim. Biophys. Acta 791(2): 186-197 (1984) cited in Bio. Abstract 79078413.

Reynolds, A. B. et al., Biol. Reprod. 30(3): 775-786 (1984) cited in Bio. Abstract 78039386.

Kayama, K. et al., J. Reprod. Immunol. 5(3): 135-144 (1983) cited in Bio. Abstract 77023274.

Wolf, D. P. et al., Biol. Reprod. 29(3): 713-724 (1983) cited in Bio. Abstract 77063608.

Isojima, S. et al., Clin. Exper. Immunol. 49(2): 449-456 (1982) cited in Bio. Abstract 75084094.

Shigeta, M. et al., Clin. Exper. Immunol. 42(3): 458-462 (1980) cited in Bio. Abstract 7107005.

*Primary Examiner*—Margaret Moskowitz
*Attorney, Agent, or Firm*—James C. Wray

[57] ABSTRACT

A new probe for forensic analysis of sexual assaults is disclosed. The probe is a monoclonal antibody to a new protein marker, MHS-5, in semen. Also disclosed is the hybridoma producing the antibody as well as an assay utilizing the antibody for forensic analysis of criminal evidence.

9 Claims, 6 Drawing Sheets

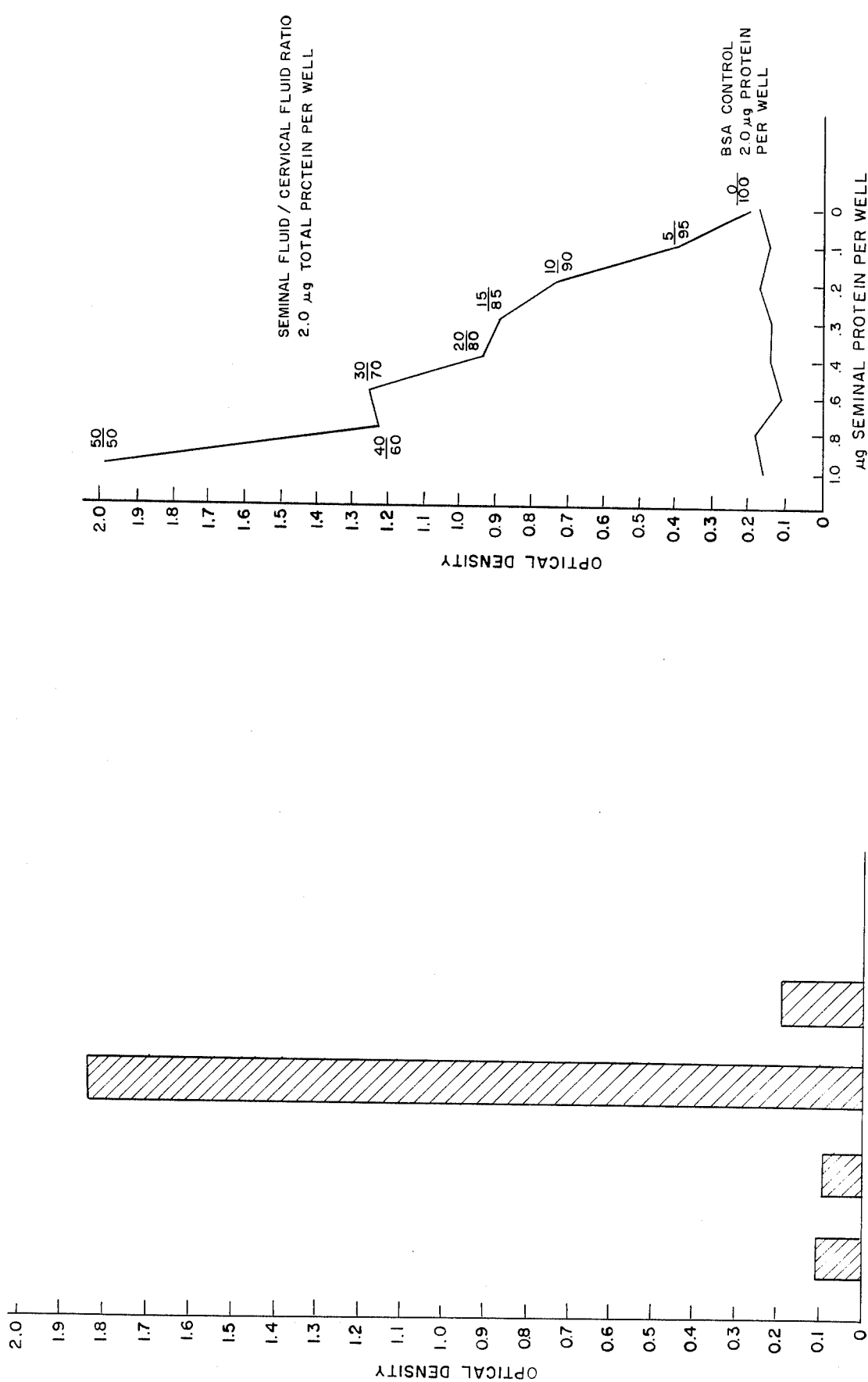

BIOLOGICAL FLUIDS TESTED FOR
MHS-5 ANTIGEN BY ELISA

| | |
|---|---|
| HUMAN SEMEN (81) | + (81) |
| HUMAN SERUM (15) | - (15) |
| HUMAN SALIVA (16) | - (16) |
| HUMAN AMNIOTIC FLUID (11) | - (11) |
| HUMAN MILK (6) | - (6) |
| HUMAN VAGINAL SECRETION (12) | - (12) |
| HUMAN CERVICAL MUCOUS (11) | - (11) |
| HUMAN NASAL MUCOUS (3) | - (3) |
| HUMAN URINE-MALE (5) | - (5) |
| HUMAN URINE-FEMALE (3) | - (3) |
| HUMAN BILE (1) | - (1) |
| HUMAN SWET (1) | - (1) |
| | |
| RABBIT OVIDUCT FLUID (1) | - (1) |
| RABBIT SEMEN (3) | - (3) |
| SHEEP SEMEN (1) | - (1) |
| DOG SEMEN (1) | - (1) |
| PIG SEMEN (1) | - (1) |
| RHESUS MONKEY SEMEN (1) | - (1) |
| CAT SEMEN (1) | - (1) |
| GOAT SEMEN (1) | - (1) |
| SQUIRREL MONKEY SEMEN (1) | - (1) |
| BULL SEMEN (1) | - (1) |
| STALLION SEMEN (1) | - (1) |
| RAT SEMINAL VESICLE FLUID (2) | - (2) |
| MOUSE SEMINAL VESICLE FLUID (3) | - (3) |
| GORILLA SEMEN (1) | + (1) |
| CHIMPANZEE SEMEN (3) | + (3) |
| ORANGUTAN SEMEN (1) | + (1) |

FIG. 10

MONOCLONAL ANTIBODY TO MHS-5: A NEW PROBE FOR SEXUAL ASSAULT ANALYSES

BACKGROUND OF THE INVENTION

This invention pertains to apparatuses and methods in the field if immunology. More in particular, the invention pertains to genetic engineering, hybridomas and monoclonal antibodies. Furthermore, this invention relates to forensic methods used in analyzing sexual assault evidence.

Current analyses of sexual assault evidence involves testing for prostatic acid phosphatase (F. M. Poyntz and P. D. Martin, *Forensic Sciences International*, 24, 17, (1984)), prostatic antigen (G. F. Sensabaugh, *J. Forensic Sci.* 23, 106 (1978)), and microscopic evidence of spermatozoa. These tests are employed for the positive identification of human semen found in and around the sexual assault victim. The test for prostatic acid phosphatase has the drawback that endogenous vaginal acid phosphatase exists at such levels that the upper limit of the range in vaginal acid phosphatase concentrations overlaps with the lower limit of the range of seminal fluid acid phosphatase (R. E. Gaensslen, *Sourcebook in Forensic Serology, Immunology and Biochemistry*, U.S. Department of Justice, Washington, D.C. (U.S. Government Printing Office, 1983)). Furthermore, a number of materials having plant origin give high acid phosphatase values. Moreover, the acid phosphatase activity of seminal stains declines by 50 to 80 percent when stored at room temperature for several months. For these reasons the assay for acid phosphatase is considered by forensic specialists to be a presumptive rather than a diagnostic assay for semen;

The microscopic identification of spermatozoa in sexual assault cases is a method hampered by the age of the evidence and the adherence of spermatozoa to material comprising criminal evidence. These difficulties often result in the failure to identify spermatozoa.

Prostate specific antigen, p30, a 32 kilodalton protein of prostatic origin, has been identified with polyclonal antisera since 1978 (G. F. Sensabaugh, *J. Forensic Sci.* 23, 106 (1978); H. Graves, G. F. Sensabaugh and E. T. Black, *New England J. Med.* 312 (6) 338 (1985)). In current forensic practice this is semen specific marker offers some advantages over protatic acid phosphatase and is widely employed (F. M. Poyntz and P. D. Martin, *Forensic Sciences International*, 24, 17 (1984); G. F. Sensabaugh, *J. Forensic Sci.* 23, 106 (1978)). A monoclonal antibody to p30 is available, however its application to forensic casework has not been reported (A. E. Frankel, R. V. Rouse, M C. Wang and T. M. Chu, *Cancer Research* 42, 3714 (1982)).

The prostate is one of two male accessory organs which contribute secretions to the ejaculate volume. The prostate contributes 15 to 30 percent and the seminal vesicles contribute 50 to 80 percent of the ejaculate volume (T. Mann and C. Lutwak-Mann. Male Reproductive Function and Semen, (Springer-Verlag, Berlin, 1981), p. 183). Because of their relatively large contributions to the total ejaculate volume, secretions from these organs are candidates for forensic markers.

There is a very real problem in criminal prosecutions of sexual assaults dealing with obtaining positive evidence of the sexual assault. The best positive evidence is semen identification. The problem with semen identification is the relatively small quantities present at the scene of the crime. The normal semen volume averages 3.5 mls with the usual range of 1.5 to 5.0 mils (*Clinical Diagnosis by Laboratory Methods*, Davidsohn and Henry, 15th edition, p. 1301). Logic dictates that the most advantageous candidate for forensic markers would be antigens located in that portion of the ejaculate which is most voluminous, i.e., seminal vesicles or prostate secretions. This is to maximize the probability that evidence of sexual assault will be more positively identified.

The present invention solves the problems in the prior art and does so more advantageously than any attempt to date.

SUMMARY OF THE INVENTION

The present invention centers around a new seminal fluid protein marker having its origin in the human seminal vesicles. This antigen is not present in the epididymides, or sperm contained there or more proximal to the testes. Mice were immunized with this antigen. Lymphocytes were extracted from the immunized mice and fused with myeloma cells. The resultant hybridoma produces a monoclonal antibody to the MHS-5 antigen. The monoclonal antibody is a probe for finding evidence of sexual assault where such evidence would not ordinarily be identifiable due to low quantities. The invention is a monoclonal antibody which offers the opportunity for national standards:

(a) a method for immunizing creatures having immune systems with the new forensic marker antigen MHS-5;

(b) the antibody produced by such creatures in reaction to said antigen as well as the lymphocytes which produce these antibodies;

(c) a hybridoma, being a product of said beta lymphocytes in combination with a multiple myeloma cell;

(d) a monoclonal antibody produced by said hybridoma;

(e) in vivo and in vitro methods of producing said monoclonal antibody with said hybridoma;

(f) an enzyme linked immunosorbent assay for detecting and positively identifying human semen utilizing the monoclonal antibody.

It is an object of this invention to provide a new probe for sexual assault analyses.

It is an object of this invention to provide a probe for sexual assault analyses which is more advantageous than previously used probes.

It is an object of this invention to provide a description of sources of antigens useful as forensic markers for the purposes of analyzing sexual assault evidence.

It is an object of this invention to teach how anitbodies may be made to these new forensic markers with special attention paid to teaching how monoclonal antibodies might be made.

It is a further object to provide a monoclonal antibody to a semen marker which can be a national standard for forensic standards both national and abroad.

These and other further objects of the invention will become apparent from the foregoing and ongoing description including the drawings.

BRIEF DESCRIPTION OF THE DRAWINGS

FIG. 6 is a bar graph depicting results from ELISA testing to determine if the epitope recognized by the monoclonal antibody to MHS-5 antigen is present on p30 (prostate specific antigen) or lactoferrin. The monoclonal antibody MHS-5 does not cross react with the previously described seminal fluid proteins.

FIG. 7 is a graph depicting results from ELISA testing for the MHS-5 antigen in mixtures of seminal fluid and cervical fluid. The MHS-5 antigen is still detectable in mixture of semen with cervical fluid.

FIG. 10 is a table of biological fluids which were tested for the MHS-5 antigen by the ELISA method.

DESCRIPTION OF THE PREFERRED EMBODIMENT(S)

Figure 1:
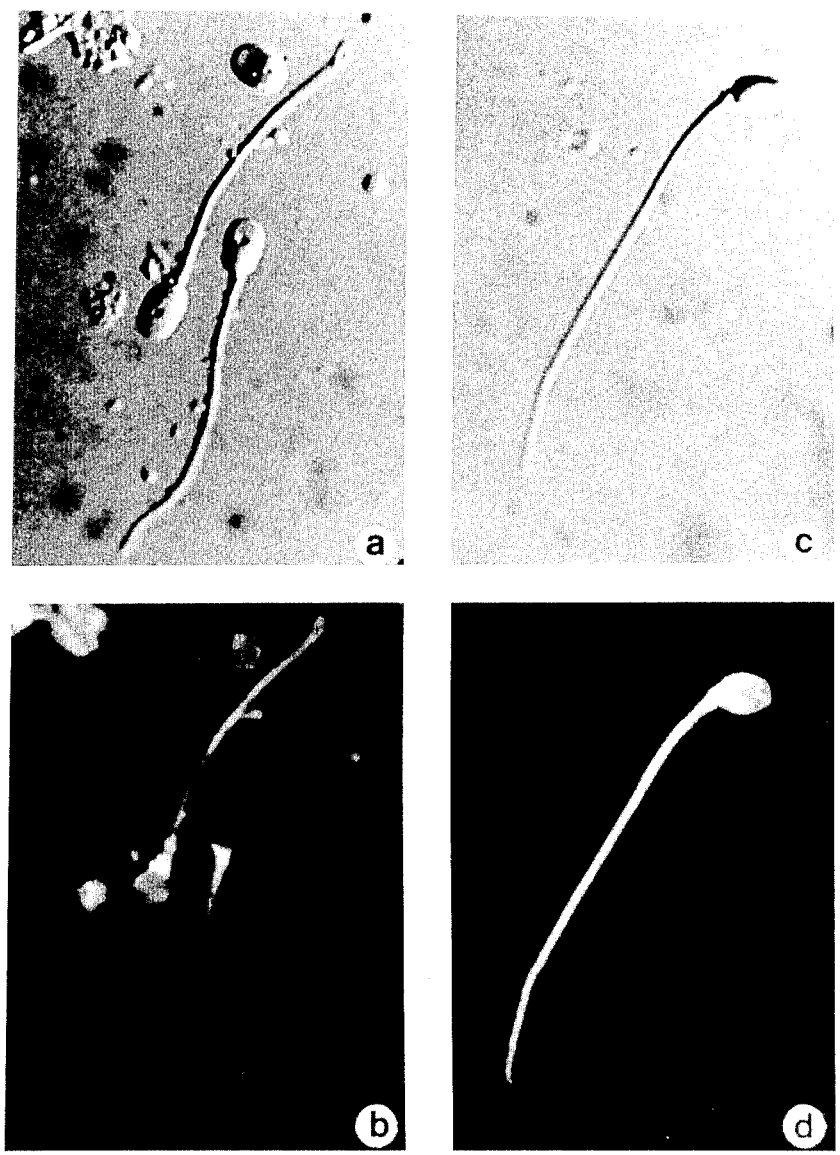
FIG. 1 shows human sperm before and after being stained with the MHS-5 (FIG. B) monoclonal antibody and polyclonal antibody (FIG. D). The differential interference contrast images of the corresponding fluorescent sperm are presented in A and C.

In 1983 there were 79,918 forcible sexual assaults against women reported in the United States (FBI Uniform Crime Reports. Crime in the United States, 1983, U.S. Department of Justice, Washington, D.C. (U.S. Government Printing Office, 1984), p.13). This figure is estimated to be one fourth to one third of the actual number of assaults committed against women. (FBI, personal communication). Additionally, 300,000 to 400,000 child molestations are estimated to occur annually. (American Humane Associations, Englewood, Colo.). The reporting of rape and child molestation and the prosecutions thereof are increasing in the United States (FBI Uniform Crime Reports. Crime in the United States 1983, U.S. Department of Justice, Washington, D.C. (U.S. Government Printing Office, 1984 p. 13). Rape, a crime of violence, is a public health issue of great importance.

From each sexual assault, mulitple pieces of evidence are obtained, consisting of materials, such as cuttings of victims clothing and undergarments, dried swabs of the vaginal, anal and oral mucosa, hair and fiber samples, scraping from solid surfaces, cloth and fabric from the crime scene. Multiple forensic tests are performed on this evidence. Among the most crucial is identification of spermatozoa and/or seminal fluid, which formally establishes the presence of semen. Establishing the presence of semen is imporant in corroborating the victim's claim of sexual assault as well as locating places at the crime scene and on the victim which contain seminal material.

Because a certain number of men are known to lack spermatozoa in the ejaculate due to aspermia, azoospermia or vasectomy, a sensitive test for small quantities of seminal fluid would be ideal to insure a positive identification of seminal material where sperm are absent. Because secretions from the seminal vesicles constitute a majority of the ejaculate, antigens or forensic markers originating in the seminal vesicles are a logical focus for any analytical device used to positively identify semen. In accordance with this logic, an antigen originating in the seminal vesicles is the focus and hub of the present invention. Monoclonal antibodies have been produced to this anitgen and these monoclonal antibodies are new and non-obvious probes for sexual assault analyses.

Monoclonal antibodies were produced by conventional procedures (G. Galfre, S. C. Howe, C. Milstein, G. W. Butcher, J. C. Howard, Nature (London) 266, 550 (1977)). BALB/c female mice were immunized four times with $1 \times 10^7$ thrice washed human sperm in incomplete Freunds adjuvant. Each immunization amounted to three injections of 0.1 ml each, injected intramuscularly and intraperitoneally. The sperm were obtained from blood type O donors. After fusion of the mouse spleen cells with the myeloma cell line SP2/0 (M. Schulman, C. D. Wilde and G. Kohler, Nature (London) 279 269 (1978)), cells were distributed into 96 well plates containing HAT selection medium. HAT selection medium comprises hypoxanthine, aminopterin, and thymidine. Screening for antibodies was performed 14 to 21 days after fusion by enzyme linked immunosorbent assays.

Enzyme linked immunosorbent assay, deemed ELISA, is an immunochemical technique. This method depends on conjugation of an enzyme to antibody which is directed at a cellular, tissue anitgen or an antigen absorbed to a solid surface. The resulting conjugate is then both immunologically and enzymatically active. Thereafter the principles are entirely analogous to those underlying the direct or indirect immunofluorescence technique which is well known in the art. Horse radish peroxidase is often the enzyme chosen for coupling to antibody. Tissues are first stained directly with antibody enzyme conjugate or indirectly with enzyme linked antiglobulin reagent following incubation with unlabeled immune serum. Thereafter, the tissue is incubated with the substrate for the enzyme. The enzyme may be detected visually for a formation of a brown or blue color after incubation with hydrogen peroxide and diamino benzedine, or ABTS.

Screening for antibodies was performed 14 to 21 days after fusion by ELISA employing $1 \times 10^5$ sperm target cells per well. Hybridomas that elicited positive binding to sperm were expanded and cloned by the limiting dilution method (G. Galfre, S. C. Howe, C. Milstein, G. W. Butcher, J. C. Howard, Nature (London) 266, 550 (1977)). Twenty-five stable IgG secreting antisperm hybridoma lines were established. To determine if the monoclonal antibodies recognized anitgens present in sperm free seminal fluid, culture supernatants from these lines were screened by ELISA for binding to normal, healthy male seminal fluids. The normal healthy male seminal fluids had sperm removed by centrifugation. The microtiter wells contained ten micrograms of protein per well. Nine monoclonal antibodies were found to bind to normal sperm free seminal fluid. These antibodies were then screened against vasectomized donors' seminal fluids, which lack not only sperm but also antigens originating in the testes or epididymides. Five monoclonal antibodies were reactive with seminal fluid from vasectomized men.

One of these five hybridomas, ATCC-HB 8830, on deposit at 12301 Parklawn Drive, Rockville, Md. produced an antibody of the immunoglobulin subclass IgGI that bound to seminal fluids from all 161 donors tested by ELISA method, including 21 semen samples from vasectomized men. No ejaculate has yet been found which did not test positive for the MHS-5 antigen. These results indicated that the monoclonal antibody fills an important criteria of a forensic marker for human semen, vis-a-vis, the recognition of an antigen present in all semen specimens tested. The finding of the MHS-5 antigen in both vasectomized semen and on washed ejaculated sperm, suggested that the epitope recognized by the antibody originated from the male reproductive tract distal to the midportion of the vas deferens, the site for vasectomies, and then bound to the sperm upon ejaculation.

Indirect immunofluoresence techniques were used to study ejaculated spermatozoa. Ejaculated spermatozoa from normal men were first incubated with the mouse monoclonal antibody to MHS-5 antigen. Following removal of non-bound antibody, a secondary antibody was then incubated with the ejaculated spermatozoa having the mouse monoclonal antibody to MHS-5 antigen. This secondary antibdoy was IgG anti-mouse antibody having a fluorescent tag. The non-bound secondary antibody was removed and the ejaculated spermatozoa were then examined microscopically for localizaton of the MHS-5 antigen. FIG. 1 presents photographs of the indirect immunofluorescent technique using polyclonal antisera to sperm in sections C and D and monoclonal antibody to angiten MHS-5, A and B. Referring to FIG. 1, the differential interference contrast, Nomarski, images of the spermatozoa, A and C, are presented above the fluorescent images, B and D.

Incubation with the monoclonal antibody to MHS-5 antigen resulted in intense staining of the post, acrosomal, midpiece and tail regions of the sperm with lesser staining of the acrosome (FIG. B). To carry out the method, $1 \times 10^5$ sperm were added to wells of eight well microslides and then air dried. Sperm were bathed with one percent bovine serum albumin in phosphate buffered saline for 30 minutes. Slides were washed three times in phosphate buffered saline. Ascites fluid containing the monoclonal antibody to MHS-5 anitgen was diluted 1:50 and then added to each well for 30 minutes. The slides were then wased five times in phosphate buffered saline. Fluorescein isothiocyanate—goat antimouse immunoglobulin at 1:150 dilution was added to the slides and incubated for 45 minutes. The slides were then washed three times with phosphate buffered saline and then mounted with a drop of glycerol. The photography was performed with a light microsocpe (Leitz) equipped with a 100x-13.2NA flotar objective.

As is stated above, intense fluorescence of the post-acrosomal, midpiece and tail regions with lesser staining of the acrosome shown in FIG. 1B was observed. This pattern occurred in 90 percent of the sperm from each donor and was not altered by methanol fixation. The number of donors was five. A polyclonal mouse anti-sperm sera from an immune animal used to perform the hybridoma fusions was used as a positive control. See FIG. 1D. The negative controls were: (1) incubation with preimmune mouse sera, diluted to an immunoglobulin concentration comparable to the cultural supernatants; (2) PBS; and (3) cultural supernatants found in the SP2/0. None of the negative controls were positive for immunofluoresence of the sperm.

Figure 2:
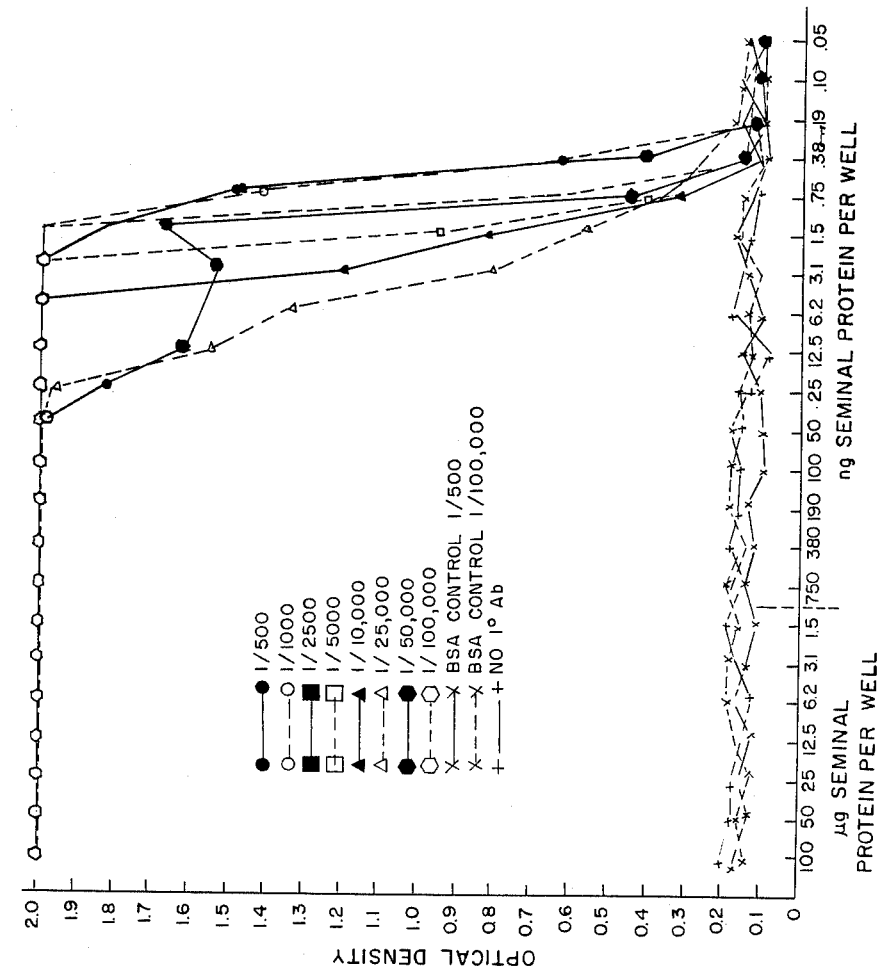
FIG. 2 shows a graph depicting results from enzyme linked immunosorption assay (ELISA) wherein seminal fluid protein concentrations and dilutions of the monoclonal antibody were varied. MSH-5 binding to seminal fluid is compared to binding to bovine serum albumin.

Ascites fluid containing high concentrations of the mouse monoclonal antibody to MHS-5 antigen was produced, pooled and titered against human seminal fluid using an ELISA assay. Concentrations of seminal fluid proteins coated onto microtiter plates and the mouse monoclonal antibody to MHS-5 anitgen were varied. FIG. 2 presents a graph depicting the results of the above outlined test. The method of FIG. 2 is as follows. Sperm free seminal fluid from a pool of normal donors was coated on the microtiter wells using a series of dilutions ranging from 100 micrograms per well to 0.05 nanograms per well. The volume added to each microtiter well was the same, being 100 microtiters. Concentration of the monoclonal antibody to MHS-5 antigen in the ascites fluid ranged from 1/500 to 1/100,000. Peroxidase labeled goat anti-mouse IgG at a dilution of 1/1,000 was used as a secondary antibody. The substrate 2,2-azino-di-(3-ethylbenzthiazolene sulphonic acid), ABTS, was used to develop a colored reaction. The optical density of the colored reaction was read on a microtiter multiscan MC apparatus after 30 minutes of incubation. Controlled bovine serum albumin, coated on an identical protein concentration range was not found to be reactive with the monoclonal antibody to MHS-5 antigen diluted 1/500 or 1/100,000. Optical density readings twice the BSA coated negative control wells were scored as positive. Using this concentration all eight dilutions of monoclonal antibody to MHS-5 antigen tested were found to be positive down to 1.5 nanograms of seminal fluid protein per well. A 1/100,000 dilution of monoclonal antibody was chosen for future ELISA experiments. At this dilution, 0.75 nanograms of seminal fluid protein per well could be identified. As was stated above, dilutions of the monoclonal antibody ascites fluid out to 1/1000,000 gave optical density readings of two or greater on plates coated with solutions containing as little as 1.5 nanograms of seminal protein per well. The upper limit of the microtiter multiscan apparatus is a maximum absorbence (O.D.) of 2. Negative control plates coated with bovine serum albumin, BSA over the same concentration range or plates which were not coated with primary antibody gaven OD readings from 0.1 to 0.2. This was done to assess the non-specific binding of the secondary antibody. Using the criterion of OD readings twice the BSA coated control well readings as the standard for a positive identification, this ELISA assay was sensitive enough to identify semen coated down to 0.75 nanograms of seminal fluid protein per well.

Figure 3:
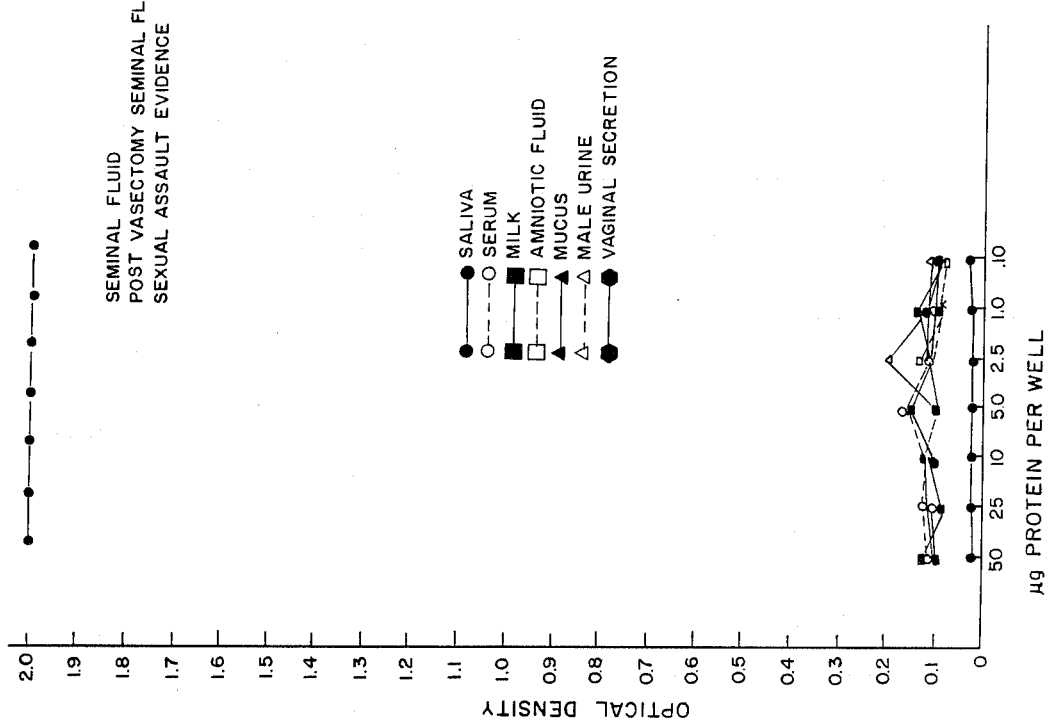
FIG. 3 shows a graph depicting results from ELISA testing of seminal fluid, post vasectomy seminal fluid, sexual assault evidence and various biological fluids for the presence of the MHS-5 antigen. The MHS-5 antigen is not found in any biological fluid other than semen.

Investigations were undertaken to determine whether the epitope recognized by the monoclonal antibody to MHS-5 antigen was present in any other human biological fluid. To carry out this test, the ELISA method in conjunction with antigen coated plates was utilizied. Referring to FIG. 3, the graph depicts results from an ELISA test in which the reactivity of monoclonal antibody to MHS-5 antigen with human seminal fluid was compared to several other biological fluids coated onto microtiter plates at varying concentrations of protein. The monoclonal antibody used was that contained in ascites fluid and was employed at a 1/100,000 dilution. After protein determinations by the method of Bradford, (M. Bradford, *Anal. Biochem.* 72, 248 (1976) serum, saliva, milk, amniotic fluid, mucous, male urine, vaginal secretion, sexual assault evidence, seminal fluid from normal donors and seminal fluid from vasectomized donors were coated on microtiter wells at concentrations of 50 micrograms of protein per well to 0.1 microgram of protein per well. ELISA was performed as described above in connection with FIG. 2. Seminal fluid from normal and vasectomized donors, as well as from sexual assault evidence, gave maximum OD readings at all protein concentrations tested and were scored as positive for the MHS-5 antigen. The other biological fluids gave OD readings equal to the bovine serum albumin control values and were scored as negative for the MHS-5 antigen. Of particular forensic interest is the finding that the MHS-5 antigen could not be detected in human serum, saliva, vaginal protein, cervical mucous and human milk. These biological fluids may be assumed to be relatively common contaminants of presumptive seminal stains.

FIG. 10 is a table summarizing the biological fluids which have been examined by ELISA for the presence of the MHS-5 antigen. Because the MHS-5 antigen has been undetectable in any other human biological fluid tested by plate coating ELISA, the monoclonal antibody to MHS-5 fulfills another important criteria of a forensic semen probe, vis-a-vis, semen specificity.

Monoclonal antibody to MHS-5 antigen has been tested on non-human primate semen samples. It has been found that the antigen is not present in rhesus monkeys, *Macca mulatta* or squirrel monkeys, genus Saimiri, but was found in gorillas, chimpanzees and orangutans. (See FIG. 10). The levels of the antigen in these Pongidae species appears to be comparable to levels in human semen. This data is not shown. It is of evolutionary interest to find this antigen in several Pongids which are close human relatives and not in members of more distantly related primate species. Although the ideal forensic semen marker should be one which cross reacts with no other animal semen, the likelihood of Pongid primates being considered rape suspects, other than in a metaphorical sense, is slight and the cross reactivity with semen of closely related primates should not detract from the application of the monoclonal antibody in forensic analysis of sexual assault evidence.

Investigations were undertaken to identify the tissues containing the anitgen MHS-5. Homogenates were made of various reproductive tract organs obtained at autopsy. Tissues were obtained within several hours of death to minimize necrosis and antigen autolysis or displacement. No attempt at preselection of autopsy material was made and specimens from patients who died from a variety of diseases were tested. There was no upper limit placed on the age of the patient but all patients were post-puberty. Protein determinations were made on these homogenates and they were plated for ELISA. Since earlier studies showed that vasectomized semen contain the antigen, it was possible that the prostate and seminal vesicles were sources for the antigen. Another possibility was that the antigen orginated both distal and proximal to the ligation point of the vas deferens, and was secreted by epididymis or testis as well as prostate or seminal vesicles.

Figure 4:
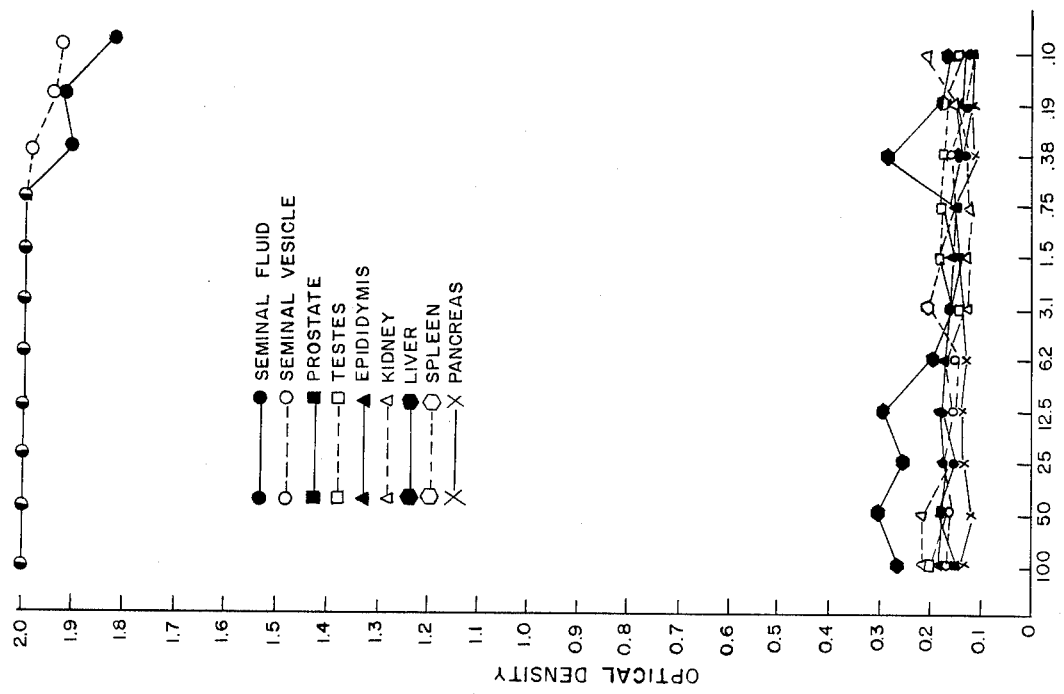
FIG. 4 is a graph depicting results from ELISA testing seminal fluid from normal donors and tissue homogenates from seminal vesicle, prostate, testes, epididymis, kidney, liver, spleen and pancreas. The MHS-5 antigen was found to localize in the seminal vesicles.

Referring to FIG. 4, results of assays for the MHS-5 antigen in these homogenates of reproductive organs from ten autopsies are presented. The data used in FIG. 4 are the results from ELISA testing of tissue homogenates from seminal vesicle, prostate, testis, epididymis, kidney, liver, spleen and pancreas. Autopsy tissues were obtained from ten cadavers and homogenized in carbonate-bicarbonate buffer, pH 9.2, using a precision scientific tissue homogenizer. The homogenates were centrifuged for ten minutes at $500 \times G$ to pellet particulate material and the solubule proteins were precipitated using cold acetone in a 10/1 ratio. A pellet of the precipitated proteins was obtained after ten minutes of centrifugation at $500 \times G$ and was resuspended in carbonate-bicarbonate buffer, pH 7.2. After protein determination by the Bradford method, proteins were coated in microtiter wells over the concentration range of 100 micrograms per well to 0.1 micrograms per well. ELISA was then performed. Mean values for ten specimens were determined and are expressed as single points on the graph. Seminal fluid from normal donors and seminal vesicle homogenate from all ten cadavers gave OD readings circa 2.0 and are scored as positive for the MHS-5 antigen. None of the other tissue homogenates tested gave OD readings greater than the background level and all were scored as negative for the MHS-5 antigen.

To summarize, seminal vesicle homogenates gave OD readings of 2 whereas homogenates of other reproductive tract organs gave OD readings similar to the background control values, as shown in FIG. 2, indicating the MHS-5 antigen originates in the seminal vesicle.

To further verify the specificity of the monoclonal antibody for seminal vesicles, homogenates were made of kidney, pancreas, spleen and liver, which upon assay gave background OD readings, indicating absence of the MHS-5 antigen. These findings indicate the organ of origin or the MHS-5 antigen is the seminal vesicles, lending additional support to the appropriateness of the monoclonal antibody to MHS-5 as a forensic probe. Because the seminal vesicles contribute 50 to 80 percent of the ejaculate volume, the MHS-5 antigen may prove to be present in relatively high concentration in the ejaculate.

Figure 5:
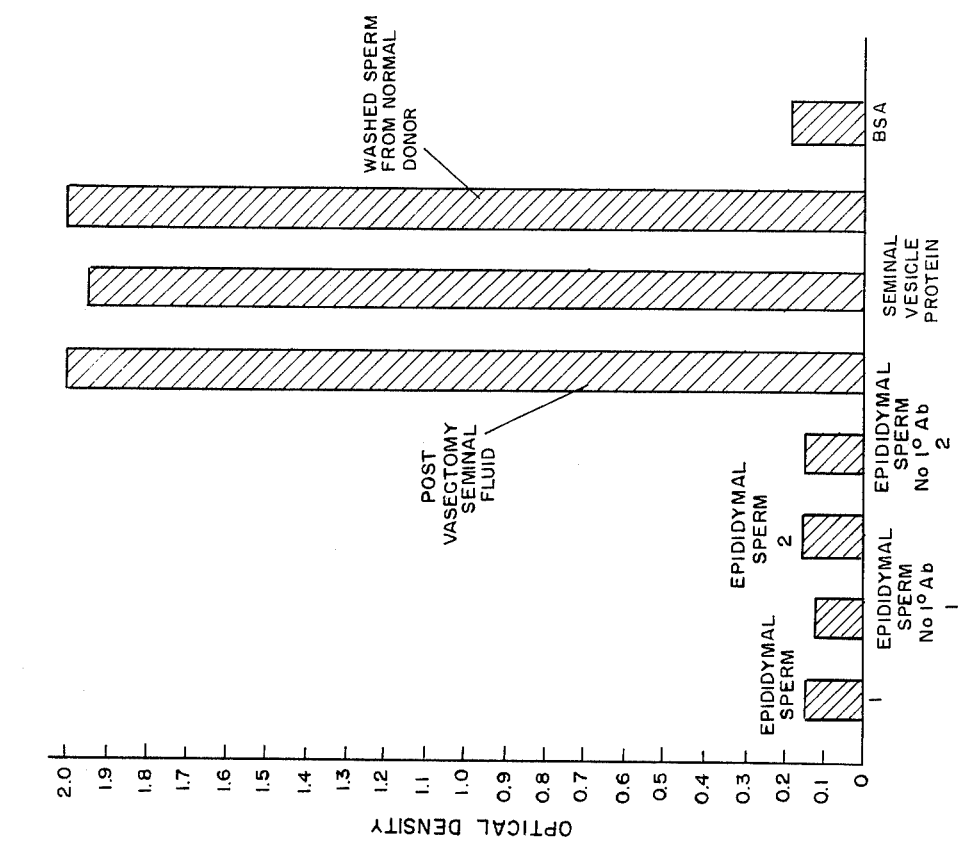
FIG. 5 is a bar graph depicting results from ELISA testing for the presence of the MHS-5 antigen on epididymal sperm obtained by vasovasostomy and orchiectomy. Although present on ejaculated sperm the MHS-5 antigen is absent on epididymal sperm.

Investigations were undertaken to specifically study the MHS-5 antigens association with epididymal sperm. Samples from the cauda epididymis were obtained from one patient at the time of vasovasostomy and another patient during orchiectomy. These sperm were plated in microtiter plates at the same concentration of ejaculated sperm, vis-a-vis $1 \times 10^5$ per well, and the binding of the monoclonal antibody to the MHS-5 antigen to the two populations of sperm was compared. Referring to FIG. 5, the results of the tests are depicted. Point 1 in FIG. 5 refers to epididymal sperm obtain at vasovasoctomy and point 2 refers to epididymal sperm obtained from orchiectomy. Twice washed epididymal sperm were coated on microtiter wells at $1 \times 10^5$ sperm per well. ELISA was performed as described in connection with FIG. 2. Sperm from normal donors, $1 \times 10^5$ sperm per well, seminal fluid from vasectomized donors, 100 microgram of protein per well, and homogenate from autopsied seminal vesicles, 100 microgram of protein per well, were used as positive controls. BSA, 100 microgram of protein per well, was the negative control. The bindings of the secondary antibody in the absence of the primary antibody is also expressed. The epididymal sperm from both patients gave optical density readings equal to the negative controls and were scored as negative for the MHS-5 antigen. Ejaculated sperm, post-vasectomy seminal fluid, and seminal vesicle homogenate all were positive for the MSH-5 antigen. As was noted above, epididymal sperm, as well as the epididymal homogenate noted above, gave optical density readings similar to the BSA coated control wells. This indicates that epididymal sperm lack the MHS-5 epitope. This is compared to the ejaculated sperm which gave high optical density readings indicating the presence of the MHS-5 antigen.

Earlier work demonstrated that lactoferrin is a sperm coating anitgen of human seminal vesicle origin (A. Hekman and P. Rumke, Fertil. Steril, 20, 312 (1969); T. K. Roberts and B. Boettcher, J. Reprod. Fert. 18, 347 (1969)). Investigations were undertaken to determine if the monoclonal antibody to MHS-5 antigen demonstrated any cross reactivity with lactoferrin or with the well known prostate marker 30. The investigations comprised a cross reactivity study of the monoclonal antibody to the MHS-5 anitgen with purified p30, prostate specific antigen, and human milk lactoferrin. FIG. 6 shows the results of this assay. FIG. 6 depicts results from ELISA to determine if the epitope recognized by the MHS-5 monoclonal antibody is present on p30 or lactoferrin. Purified p30 and lactoferrin were coated on microtiter wells at 20 micrographs per well along with cooled seminal fluid from normal donors, positive control, and BSA, negative control, at the same concentration. Both the p30 antigen and the lactoferrin gave optical density readings no higher than the BSA negative control and were scored negative for the MHS-5 antigen. Pooled seminal fluid gave typically high optical density readings and were scored as positive for the MHS-5 antigen. No cross reactivity of the MHS-5 monoclonal antibody and these previously characterized seminal proteins was observed.

Investigations were undertaken to discover if the MHS-5 antigen was masked or rapidly degraded in the presence of vaginal or cervical proteins. Seminal proteins were mixed with vaginal secretions and cervical mucous and then tested for the presence of the MHS-5 antigen. A pool of vaginal cervical protein from ten individuals was made. Various ratios of seminal portein to vaginal/cervical protein were prepared, allowed to incubate together for four hours at 37° centigrade, and then analyzed by ELISA. Typical results from these experiments is depicted in the graph of FIG. 7. Seminal fluid and cervical fluid of known protein concentration were mixed in varying ratios from 50/50 to 0/100, seminal/cervical. After incubation at 37° centigrade for four hours, 2.0 micrograms of each mixture was coated in microtiter wells and ELISA was performed as described in connection with FIG. 2. Optical density readings greater than twice the BSA negative control were obtained with all seminal fluid/cervical fluid ratios tested. These results indicate that this assay has the ability to identify 0.1 microgram of seminal protein in a mixture of cervial fluid and seminal fluid in a ratio of 19/1. Cervical fluid alone gave optical density readings equal to the BSA negative control. In such mixtures after four hours of incubation, it was possible to detect as little as 0.1 microgram of total seminal protein in 1.9 microgram of vaginal protein, 19/1 ratio. This in vitro study: (1) showed that the antigen was not masked in the presence of proteins from the female tract; (2) provided evidence that the MHS-5 epitope remains stable over time in the presence of female tract secretions. This evidence suggests that the MHS-5 antigen may fulfill another important criterion for a forensic seminal marker, namely, persistence in the female tract following insemination.

Semen has been subjected to several treatments in an attempt to alter antibody binding to the ELISA. The following treatments of human semen have not altered the abiltiy of the monoclonal antibody to the MHS-5 antigen at a 1/100,000 dilution of the ascites fluid containing the monoclonal antibody to bind seminal fluid coated plates with ten micrograms per well: (1) heating at 65° centigrade or boiling at 100° centigrade for two hours; (2) treatment at pH 1.8 for 12 hours; and (3) freezing in liquid nitrogen for 16 hours. In addition, it was found that incubation of semen in 5 milligrams per ml of pepsin for 12 hours at pH 1.8 eliminated binding of the monoclonal antibody to MHS-5 antigen to its epitope. Together these findings show that the monoclonal antibody to the MHS-5 anitgen recognizes a pepsin sensitive epitope which is resistant to boiling (thermostable).

Figure 8:
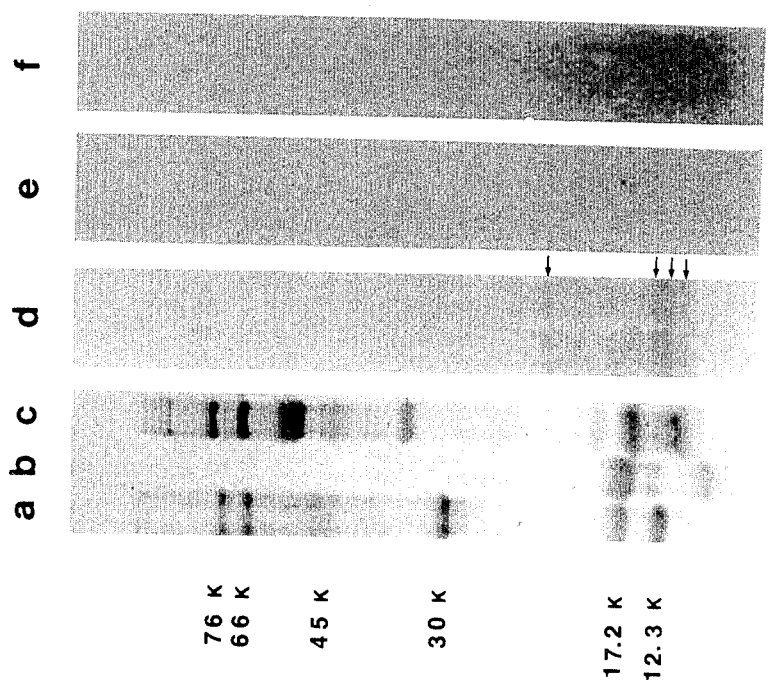
FIG. 8 is a photograph of an immunoblot localization of polypeptides reacting with the monoclonal antibody to MHS-5.
Figure 9:
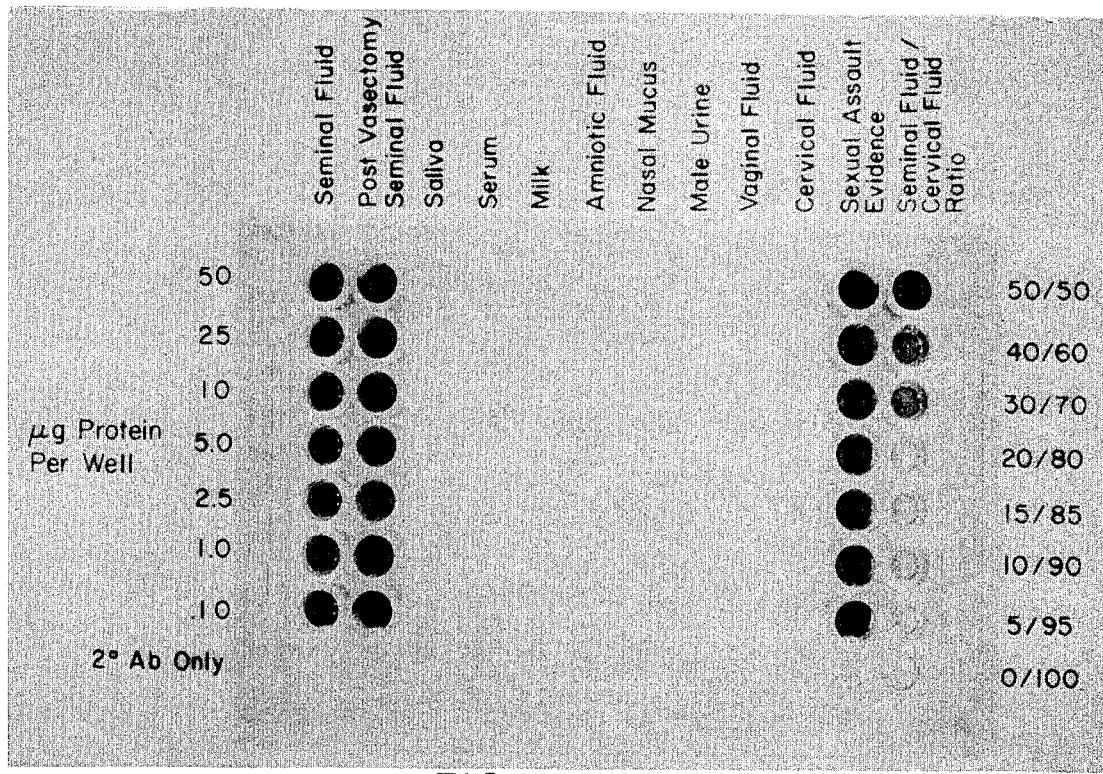
FIG. 9 is a photograph of an ELISA assay showing positive and negative reaction in microtiter wells.

To further characterize the chemical nature of the molecules bearing the MHS-5 epitope, proteins from the semen of vasectomized men following semen liquifaction were separated on 12 percent SDS-polyacrylamide gels, 16 cm, in the presence of B-mercaptoethanol, reduced, and electro-transferred to nitrocellulose for immunolocalization. FIG. 8 is a photograph of immunoblot localization of polypeptides reacting with the monoclonal antibody to MHS-5 antigen. Seminal fluid from vasectomized donors was allowed to liquify at room temperature for 30 to 60 minutes. The sample was diluted in PAGE sample buffer. The buffer consists of 50 millimoles of tris-HCL, pH 6.8, 2 percent SDS, 1.0 percent glycerol, 1.0 percent mercaptoethanol, and 0.2 millimoles of PMSF. The dilution of the sample in the buffer was 1 milligram to 1 ml. The dilution was heated in boiling water for five minutes. 30 micrograms of sample was loaded into each lane and electrophoresed at 10 milliamps constant current and subsequently electro-transferred to nitrocellulose paper at 60 milliamps for 12 to 18 hours. Portions of the nitrocellulose were cut and stained with 0.1 percent amido black for molecular weight determination (see lanes a and b). Staining of the nitrocellulose was also to demonstrate the distribution of total protein remaining in the seminal fluid following liquifaction (see lane c). The experimental nitrocellular strips were bathed in 3.0 percent BSA at 45° centigrade for two hours and then incubated in either monoclonal antibody to MHS-5, lane d, or a non-specific monoclonal antibody at the same antibody concentration in lane 3. The strips were washed extensively and subsequently incubated with HRP goat anti-mouse immunoglobulin for one hour at room temperature. The strips were again washed and the localization of the antigen components completed by incubating the strips in 0.04 percent DAB/0.015 percent H202 in tris-HCL buffer, pH 7.2. A triplet of immunoreactive bands was demonstrated with molecular weights ranging from 11.1 to 12.7 kilodaltons and an additional band at 20 kilodaltons. The control was a strip incubated in secondary antibody alone and then processed normally, lane f. Lane a of FIG. 8 shows high molecular weight standards, lane b shows low molecular weight standards. The total complement of seminal protein stained with amido black on the nicroellulose are presented in lane c. Lane d contains protein bands which reacted with monoclonal antibdoy to MHS-5 antigen on imunoblotting. A triplet of immunoreactive protein bands bearing the MHS-5 epitope was found at approximately 11.2 to 12.7 kilodaltons, p=0.99. In addition, the monoclonal bound to a component with a molecular weight of 20 kilodaltons. These major components are termed seminal fluid 11-13 and seminal fluid 20.

Investigations were undertaken to test the antibody to the MHS-5 antigen on simulated forensic evidence. Ejaculates from 15 donors were dried onto cotton cloth at room temperature. The cloth remained at ambient temperature for one week. After the cloth was cut into one centimeter squares, the proteins on the cloth were eluted in phosphate buffered saline at pH 7.2. This eluate was coated into microtiter wells. Using the standard ELISA technique described above, all of the eluates from simulated evidence samples tested positive for semen.

Thirty cuttings from actual forensic casework were obtained from the FBI. The oldest of these samples was five months and the most recent sample was one month old. All of these were collected from assault victims. Semen was positively identified in 14 of the samples by ELISA, wherein microtiter wells were coated with ten micrograms of proteins eluted in phosphate buffered saline from a one centimeter section of cloth cut from the evidence. Fourteen samples were positive for the antigen MHS-5. Spermatozoa was microscopically confirmed on 13 samples. Fifteen samples tested negative for the MHS-5 antigen. Spermatozoa were found microscopically on only one of these 15 samples. These rsults of a pilot study of forensic casework demonstrated good correlation between the microscopic identification of spermatozoa in forensic evidence and a positive score by the ELISA method using the monoclonal antibody to MHS-5 antigen.

The MHS-5 monoclonal antibody is proposed as a new forensic probe for semen on the basis of the following findings: (1) the monoclonal antibody of the present invention recognized an antigen which was present in the semen of all donors tested, including vasectomized men; (2) no cross reactivity was observed with any other human biological fluid or with the semen of certain other animals; (3) a sensitive, inexpensive enzyme-linked-immunosorption-assay, ELISA, was developed which gives a positive identifcation of semen with as little as 0.75 ng seminal fluid protein present; (4) the antigen is not masked in vaginal fluids and may be detected in mixtures of semen and vaginal fluid; (5) the antigen originates in the seminal vesicles, the major contributor of secretions to the ejaculate; (6) the antigenic epitope is thermo-stable and has been detected in forensic evidence several months old; and (7) the antigen coats the surface of ejaculated sperm.

Because the inventive monoclonal antibody does not react with human sperm obtained from the epididymis but does bind the ejaculated sperm both on ELISA assay and by immunofluorescence, the MHS-5 antigen may be categorized as a "sperm coating antigen." The monoclonal antibody to MHS-5 may therefore be useful not only as a probe for seminal fluid using ELISA or radio immuno assay, but also as a probe to search for spermatozoa on slides of forensic casework. In this case, immuno-fluorescent microscopy could be applied to produce a fluorescent micrograph of human sperm which could be used as legal evidence.

Weil, (A. J. Weil, *J. Reprod. Fertil.*, Suppl. 2, 25 (1967)), first demonstrated an antigen, termed "sperm coating antigen," which originated in the human seminal vesicles and coated the human sperm surface during ejaculation. At least six sperm coating antigens have since been identified in human seminal plasma (K. Koyama, Y, Takada, T. Takemura and S. Isojima, J. Reprod. Immunol. 5, 134, (1983)). Two of these antigens; lactoferrin (A Hekman and P. Rumke, *Fertil. Steril.* 20, 312 (1969)), also known as scafferin (T. K. Roberts and B. Boettcher, *J. Reprod. Fert.* 18, 347 (1969)), and the seminal plasma No. 7 antigen, ferrisplan, (K. Koyama, Y. Takada, t. Takemura and S. Isojima, *J. Reprod. Immunol.* 5, 134 (1983)) have been shown to originate in the human seminal vesicles and to share antigenic cross reactivity with similar proteins in human milk. The MHS-5 monoclonal antibody recognizes an epitope located on a group of proteins with an approximate molecular weight of 11–13 kd and on a larger 20 kd component. These proteins have been identified as bearers of HMS-5 epitope by immunoblot analysis of proteins from liquified ejaculates obtained from vasectomized men. These proteins have been reduced by B-mercaptoethanol and separated by SDS-PAGE. Several considerations suggest that the MHS-5 antigen is a unique seminal vesicle protein distinct from either lactoferrin (A. Hekman and P. Rumke, *Fertil. Steril.* 20, 312 (1969)) or No 7 antigen (K. Koyama, Y, Takada, T. Takemura and S. Isojima, *J. Reprod. Immunol.* 5, 134 (1983)). Among these considerations is the fact that human seminal lactoferrin, when electrophoresed in a Laemmli system similar to that used in this study, has an apparent molecular weight of 80 kilodaltons (G. F. Sensabaugh, *J. Forensic Sci.* 23, 106 (1978)). Likewise, seminal plasma No. 7 antigen, when electorphoresed under reducing conditions, has a molecular weight of 15 kilodaltons (S. Isojima, K. Koyama and N. Fujiwara, *Clin. Exp. Immunol.* 49, 449 (1982)). Thus, neither of these previously described seminal fluid antigens of seminal vesicle origin has the same molecular weight as the 11–13 kd immunoreactive triplet or the 20 kd higher molecular weight form. Further, antisera produced to lactoferrin or to semnal plasma No. 7 antigen have shown cross reactivity with similar proteins in human milk (T. K. Roberts and B. Boettcher, *J. Reprod. Fert.* 18, 347 (1969); (K. Koyama, Y. Takada, T. Takemura and S. Isojima, *J. Reprod. Immunol.* 5, 134 (1983)). The MHS-5 monoclonal antibody, on the other hand, gave background OD readings on all human milk samples tested and failed to bind to purified milk lactoferrin. In a recent report, a protein immunologically related to a rat seminal vesicle protein (SVS-IV) was detected in human seminal fluid (P. Abrescia, G. Lombardi, M. DeRosa, L. Quagliozze. J. Guardiola, and S. Metafora, *J. Reprod. Fert.* 73, 71 (1985)). SVS-IV has been reported to have a molecular weight of 17 kilodaltons (M. C. Ostrowski, M. K. Kistler and W. S. Kistler, *J. Biol. Chem.* 254, 383 (1979)), considerably higher than the major protein group recognized by the MHS-5 monoclonal antibody. Thus, when compared to a previously described human seminal vesicle antigens, the 11–13 kd and 20 kd protein groups recognized by the MHS-5 monoclonal antibody represent a novel seminal fluid antigenic marker. The forensic markers currently in use, p30 and acid phosphatase, are secretory products of the prostate gland. To our knowledge, the MHS-5 antigen is the first maker protein from the human seminal vesicles which has been proposed for forensic application.

Analyses of human semen by 2-D gels (J. J. Edwards, S. L. Tollaksen and N. G. Anderson, *Clin. Chem.* 27 (8), 1335 (1981)) and by a 1-D SDS-PAGE of split ejaculate fractions (M. Balerna, G. M. Colpi, D. Leonardi and A. Campana, *Andrologia* 16 (4), 350 (1984)), have shown that seminal fluid contains several families of major proteins in the 10–25 K-dalton range. These proteins are found in the final or seminal vesicle portion of the ejaculate (M. Balerna, G. M. Colpi, D. Leonardi and A.

Campana, *Andrologia* 16 (4),350 (1984)) and show changes in molecular weight during semen liquifaction (17). It is possible that the heterogeneity of mass exhibited by the polypeptides which bear the MHS-5 epitope is due to isoforms generated during semen gelation or liquifaction.

The monoclonal antibody to MHS-5 did not bind to purified prostate specific antigen, PSA or p30, by the ELISA method. When the MHS-5 monoclonal antibody was incubated with nitrocellulose blots containing seminal fluid proteins from vasectomized men, the monoclonal did not bind to any protein with a molecular weight similar to p30 which is about 32 kilodaltons, notwithstanding a prominent protein band, at 32 kd, presumably p30, being visible on a protein stain of the blot. These findings indicate that MHS-5 is directed to a seminal fluid marker protein distinct from p30.

Boiling seminal fluid for two hours prior to coating for ELISA did not decrease the binding of MHS-5 antigen to the boiled preparation when compared to non-boiled seminal fluid. Pepsin treatment of seminal fluid prior to binding to the plate eliminated subsequent recognition by the monoclonal antibody to MHS-5. Because pepsin initiates hydrolysis of proteins at peptide bonds involving the carboxyl group of aromatic amino acids, but does not degrade carbohydrate which might be associated with a protein, the pepsin sensitivity of MHS-5 binding suggest the epitope recognized by the monoclonal antibody to MHS-5 is likely a proteinaceous domain.

The MHS-5 hybridoma has demonstrated continued immunoglobulin secretion in culture for six months and has been frozen and recovered repeatedly. Three separate groups of mice have produced monoclonal antibody ascites with this clone, averaging 27 mg IgG/ml. Using the criterion for positivity of an OD greater than twice the background OD, each of these ascites samples demonstrated titers greater than 1:50,000 on wells coated with 10 ug seminal fluid protein. Thus, ATCC-HB 8830 has demonstrated its stability and shown adequate levels of immunoglobulin secretion as an ascites tumor. Good yields from a scaled up production of this monoclonal antibody can be expected.

The advantages of monoclonal immunoreagents over their polyclonal counterparts are their properties of uniformity, specificity, constant affinity and avidity, and their availability in virtually unlimited supply. These features of monoclonal antibodies make their application in forensic science particularly attractive. Perhaps nowhere is the need for a standard immunoreagents more apparent than in the field of forensic science where assays requiring high sensitivity and reproducibility are the mainstay of criminal evidence. Such tests have immediate consequences for victim treatment and the judicial system.

A survey of the forensic literature suggests monoclonal antibodies have not heretofore found wide forensic application. Use of monoclonal antibodies may standardize immunoassays performed in forensic laboratories giving an added measure of certainty to testimony by the forensic specialist. Because the monoclonal antibody to MHS-5 recognizes a protein marker distinct from the prostate marker p30, future management of forensic casework could employ immunological probes for both these seminal markers.

As this invention may be embodied in several forms without departing from the spirit or essential characteristics thereof, the present embodiment is therefore illustrative and not restrictive, and since the scope of the invention is defined by the appended claims, all changes that fall within the metes and bounds of the claims or that form their functional as well as conjointly cooperative equivalents are therefore intended to be embraced by those claims.

What we claim as our invention is:

1. A probe for sexual assault analyses, comprising, an antibody which specifically binds to a seminal fluid antigen contained in male human ejaculate wherein said antibody has no cross reactivity with other human biological fluids, semen of an animal selected from a group consisting of rabbits, sheep, dogs, pigs, rhesus monkeys, cats, goats, squirrel monkeys, bulls, stallions, rats and mice, and human epididymal sperm, wherein said seminal fluid antigen has the identifying characteristics of the MHS-5 antigen and originates in seminal vesicles.

2. The probe of claim 1 wherein said antibody is the monoclonal antibody which is the product of hybridoma ATCC-HB 8830.

3. The probe of claim 2 wherein said monoclonal antibody binds to MHS-5 present in the semen of gorillas, chimpanzees and orangutans.

4. The ATCC-HB-8830 hybridoma cell line which produces a monoclonal antibody to a seminal fluid antigen contained in male human ejaculate.

5. A method for making probes for sexual assault analyses, comprising the steps of:
 (a) culturing hybridoma ATCC HB 8830 in an in vitro culture medium or in vivo under conditions suitable for the production by said hybridoma of monoclonal antibodies; and
 (b) harvesting monoclonal antibodies generated by said hybridoma.

6. A kit for
for the analysis of sexual assault by enzyme linked immunosorbent assay comprising an antibody which specifically binds to the MHS-5 human seminal fluid antigen in a biological fluid and reagent means for detecting the binding of said antibody to the MHS-5 antigen, wherein said antibody and said means are present in amounts sufficient to perform said enzyme linked immunosorbent assay.

7. The kit of claim 6 wherein said antibody is an IgG antibody.

8. The kit of claim 7 wherein said IgG antibody is of the subclass IgGI antibody.

9. The kit of claim 6 wherein the antibody is the monoclonal antibody by hybridoma ATCC-HB 8830.

* * * * *